United States Patent [19]
Joullié et al.

[11] 3,950,387
[45] Apr. 13, 1976

[54] CYSTEINE DERIVATIVES
[75] Inventors: Maurice Joullié, Saint-Germain-en-Laye; Lucien Lakah, Paris; Gabriel Maillard, Paris; Pierre Muller, Paris, all of France
[73] Assignee: Recherches Pharmaceutiques et Scientifiques, Paris, France
[22] Filed: June 7, 1973
[21] Appl. No.: 367,821

[30] Foreign Application Priority Data
June 15, 1972 France .............................. 72.21607

[52] U.S. Cl. ....... 260/468 L; 260/294.8 G; 260/470; 260/481 R; 260/516; 260/112.5 R; 424/263; 424/309; 424/314; 424/319
[51] Int. Cl.$^2$ .......................................... C07C 69/52
[58] Field of Search ......... 260/294.8 G, 468 L, 470, 260/481 R

[56] References Cited
UNITED STATES PATENTS
3,531,490  9/1970  Friedman et al. ............ 260/294.8 G

OTHER PUBLICATIONS

Frankel et al., J. Chem. Soc., London, pp. -1390-1393, part 1, (1960).

*Primary Examiner*—Alan L. Rotman
*Attorney, Agent, or Firm*—Armstrong, Nikaido & Wegner

[57]  ABSTRACT

S-substituted cysteines, alkyl esters of S-substituted cysteines and S-substituted glutathiones in which the substituent on the S atom is allyl, geranyl, cinnamyl, benzylidene-3-butyl, 1-(para-chlorophenyl)ethyl and (pyridyl-3)methyl but excluding S-allyl cysteine bring about a reduction in atheromatic deposits in the aorta of test animals as well as a reduction in hypercholesterolemia and are of low toxicity. They may be used by the conventional routes for the treatment of human atheromatic conditions and disorders of the lipid metabolism.

8 Claims, No Drawings

CYSTEINE DERIVATIVES

This invention relates to derivatives of cysteine which carry a substituent on the sulphur atom and possibly an additional substituent on the nitrogen atom and in which the carboxyl group may be esterified, to the preparation thereof and to compositions containing the same.

It has been found that the derivatives of cysteine and glutathione which form the subject of the invention may be used for treating numerous complaints such as elastosis, elastorexia, collagenosis, degenerative arthropathy, arthrosis, arthritis, atheromatosis and arteriosclerosis.

Furthermore, the reduction in the level of blood cholesterol found in certain batches of animals treated with the cysteine derivatives of the invention indicate activity against hypercholesterolemia.

In accordance with the present invention there is provided an L cysteine or glutathione derivative having one of the general formulae $$RS-CH_2-CH(NH_2)-COOR_1$$

or $$H_2NCH(COOH).CH_2CH_2CONHCH(CH_2SR)CONHCH_2COOH$$

in which R is an allyl, geranyl, cinnamyl, benzylidene-3-butyl, 1-(para-chlorophenyl)ethyl or (pyridyl-3)methyl group and $R_1$ is a hydrogen atom or an alkyl group having 1 to 4 carbon atoms provided that when R is allyl $R_1$ is an alkyl group having 1 to 4 carbon atoms, together with salts thereof with pharmacologically acceptable organic or mineral acids.

Thus the invention includes the following compounds of the L series:

Ethyl β-(propen-2-ylthio) α-amino propanoate hydrochloride or ethyl S-allylcysteinate,
isopropyl β-(propen-2-ylthio) α-amino propanoate hydrochloride or isopropyl S-allylcysteinate,
S-allyl glutathione or γ-glutamyl-S-allyl cysteinylglycine,
S-geranylcysteine,
β-(3-phenyl-propen-2-ylthio) α-aminopropanoic acid or S-cinnamyl cysteine,
β-(4-phenyl-3-methylbuten-3-ylthio) α-aminopropanoic acid or S-(3-benzylidenebutyl)-cysteine,
β-[1-(p-chlorophenyl)ethylthio]α-amino propanoic acid or S-[1-(p-chlorophenyl)ethyl]-cysteine and
β-[(pyridyl-3)methylthio]α-aminopropanoic acid or S-[(pyridyl-3)methyl]cysteine.

In accordance with a feature of the invention the compounds are produced by a process which comprises (a) reacting cysteine or glutathione with a halide having the general formula

RX in which R is as defined above and X is a halogen or (b) esterifying a cysteine of the general formula $$RS-CH_2-CH(NH_2)-COOH$$

with an alkanol having one to four carbon atoms.

The following examples illustrate the preparation of the compounds referred to above.

EXAMPLE 1

Ethyl L β-(propen-2-ylthio) α-amino propanoate hydrochloride or ethyl S-allyl cysteinate (LJ 565).

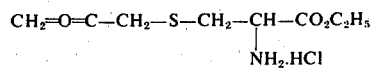

9.66 g (0.06 mole) of S-allylcysteine is added to 150 ml of anhydrous ethyl alcohol. After saturation with hydrochloric acid gas and solution of the S-allylcysteine, the mixture is refluxed for 5 hours and evaporated to dryness. The residue is dissolved in diethyl ether, filtered, and recrystallised from a mixture of 35 ml of cyclohexane and 35 ml of ethyl acetate. 9 g of product is obtained (yield 67%). M.pt = 121°C.

Analysis

The calculated and found values for $C_8H_{16}O_2NS\ Cl$ are:

C % calculated : 42.57; found : 42.32
H % calculated : 7.09; found : 7.26
N % calculated : 6.21; found : 6.28
S % calculated : 14.19; found : 14.11

Thin layer chromatography on silica gel shows that the product forms only a single spot. $R_f = 0.70$. (Solvent is a mixture of 15 parts of n-butanol, 15 of acetone, 10 of acetic acid and 20 of water).

EXAMPLE 2

Isopropyl L β-(propen-2-ylthio) α-aminopropanoate hydrochloride or isopropyl S-allylcysteinate (LJ 556).

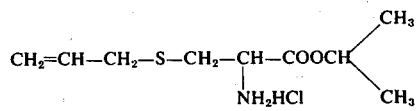

This product is prepared in accordance with the procedure described in Example 1. 9.66 g (0.06 mole) of S-allyl cysteine and 150 ml of anhydrous isopropanol are reacted with one another. The reaction mixture is refluxed for 8 hours. After washing in diethyl ether the residue is filtered and recrystallised from 75 ml of cyclohexane and 25 ml of isopropyl acetate. 9.1 g of product is obtained (yield = 63%). M.pt = 170°C.

Analysis

The calculated and found values for $C_9H_{18}O_2NS\ Cl$ are:

C % calculated : 45.09; found : 44.53
H % calculated : 7.51; found : 7.71
N % calculated : 5.84; found : 5.85

Thin layer chromatography on silica gel (in the same mixture of solvents as that used for Example 1) shows that the product forms only a single spot. $R_f = 0.77$.

EXAMPLE 3

L S-allyl glutathione or L γ-glutamyl-S-allylcysteinyl glycine (LJ 545).

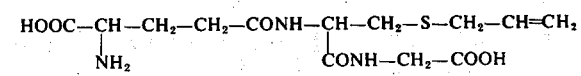

To 500 ml of liquid ammonia which has been cooled in a bath of carbon dioxide snow and acetone, is added in small portions 30.7 g (0.1 mole) of glutathione and 6.9 g (0.3 gram atom) of sodium. To this mixture is added 13.3 g (0.11 mole) of freshly distilled allyl bromide diluted in 25 ml of diethyl ether. When this reaction mixture gives a negative reaction to nitroprusside the ammonia is removed. The residue is dissolved in 200 ml of iced water containing 10% acetic acid. This solution is extracted with diethyl ether and concentrated under a pressure of 0.5 mm of mercury. A colourless syrup is obtained which solidifies in ethanol. The powdery solid is washed a number of times with 90% ethanol until free from bromide ions. The product crystallises with two molecules of water 33 g of product are obtained (yield 86%). M.pt = 148°–149°C (after softening at 108°C).

Analysis

The calculated and found values for $C_{13}H_{25}O_8N_3S$ are:

C % calculated : 40.72; found : 40.60
H % calculated : 6.57; found : 6.50
N % calculated : 10.95; found : 10.95

Thin layer chromatography reveals that the product forms only a single spot. $R_f = 0.32$ (using the same solvent as in Example 1).

EXAMPLE 4

S-geranylcysteine (LJ 558)

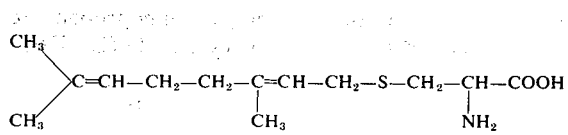

17.5 g of cysteine hydrochloride monohydrate and 6.9 g of flaked sodium are placed in 500 cm³ of liquid ammonia. After the sodium has disappeared, 28 g (6 g excess) of geranyl bromide diluted with 30 cm³ of diethyl ether is gradually added. The reaction of the thiol compound takes place during the course of a few hours.

After removing the ammonia, the residue is dissolved in 150 cm³ of distilled water and extracted with diethyl ether. The pH of the aqueous solution is raised to 6.3 using concentrated hydrochloric acid. The product is washed with water until free from chloride ions, then with alcohol and finally with ether. 19.3 g of product is obtained (yield = 75%). M.pt = 188°–189°C.

Analysis

The calculated and found values for $C_{13}H_{23}O_2NS$ are:
C % calculated : 60.73; found : 60.70
H % calculated : 9.02; found : 9.30
N % calculated : 5.44; found : 5.18

Thin layer chromatography shows that the product forms only a single spot.

EXAMPLE 5

L β-(3-phenyl-propen-2-ylthio) α-amino propanoic acid or S-cinnamylcysteine (LJ 536)

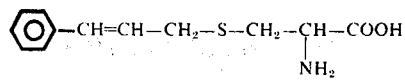

100 g (0.57 mole) of cysteine hydrochloride monohydrate and 39.3 g (1.7 gram atom) of flaked sodium are added to 1800 ml of liquid ammonia. To this mixture is added 113 g (0.58 mole) of cinnamyl bromide diluted with 200 ml of diethyl ether. When the test for the thiol group proves negative, the ammonia is removed. The residue is dissolved in two liters of iced water and, after extraction with diethyl ether, the aqueous solution is neutralised with 4 N hydrochloric acid. The precipitate is purified by solution in 4N ammonium hydroxide and filtration, followed by precipitation with 5N hydrochloric acid. The product is filtered and washed until free from chloride and bromide ions. It is then rinsed with alcohol and dried. 130 g of product are obtained (yield 84%). M.pt = 227.5° – 228.5°C (Buchi).

Analysis

The calculated and found values for $C_{12}H_{15}O_2NS$ are:
C % calculated : 60.73; found : 60.68
H % calculated : 6.37; found : 6.32
N % calculated : 5.90; found : 5.79
S % calculated : 13.51; found : 13.35

Thin layer chromatography shows that the product forms only a single spot. $R_f = 0.50$ (using the same solvent as used in Example 1).

EXAMPLE 6

L β-(4-phenyl-3-methylbuten-3-ylthio) α-aminopropanoic acid or S-(3-benzylidenebutyl) cysteine (LJ 540).

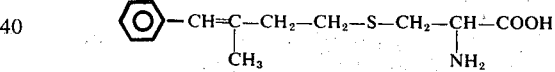

1. methyl 3-benzylidene butyrate.

150 g of 3-benzylidene-butyric acid (M.pt 110°C) which has been recrystallised from cyclohexane, is refluxed for 2 hours with a mixture of 1 kg of anhydrous methanol and 120 g of concentrated sulphuric acid. The solvent is removed, the residue dissolved in crushed ice and extracted with diethyl ether. The organic phase is washed with a solution of sodium bicarbonate, then with water, and dried over sodium sulphate. 156 g of product is obtained (yield = 96.5%). B.pt = 98°C/0.5–0.6 mm, $n_D^{20}$ = 1.5410.

2. 3-benzylidene butyl alcohol or 4-phenyl-3-methyl-buten-3-ol.

6 g of lithium aluminium hydride is added to 300 ml of tetrahydrofurane freshly distilled from lithium aluminium hydride. 44 g (0.23 mole) of methyl 3-benzylidene butyrate diluted with 100 ml of tetrahydrofurane is gradually added to this solution at +10°C whilst stirring. After the addition is completed the mixture is allowed to return to ambient temperature during the course of 50 minutes and is then held at 40°C for 90 minutes. The mixture is then cooled to 0°C and 127 ml of water at 0°C is carefully added. The mixture is filtered, rinsed with tetrahydrofurane and evaporated to dryness by means of a rotary evaporator. The residue obtained is extracted with diethyl ether and dried. The solvent is removed and the product distilled. 35.3 g of a colourless, viscous liquid product are obtained (yield = 95%). B.pt = 106°–109°C/0.2–0.3 mm, $n_D^{20}$ = 1.5664.

3. 3-benzylidene butyryl bromide.

89 g of triphenylphosphine are suspended in 290 ml of acetonitrile at +5°C. 53.5 g of dry bromine is added during 20 minutes and then a solution of 54 g (0.33 mole) of 3-benzylidene butyl alcohol in 154 g of acetonitrile is added during 30 minutes. The temperature rises to 35°C and the mixture becomes homogenous. The temperature is increased to 50°C, the solvent is removed and the residue extracted with diethyl ether. The ethereal phase is washed with a saturated solution of sodium bicarbonate, then with water, and is dried over anhydrous magnesium sulphate. 71 g of product is obtained (yield = 94.5%). B.pt = 106°–108°C/0.3–0.4 mm, $n_D^{20°}$ = 1.5820.

4. L S-(3-benzylidenebutyryl)cysteine.

68.5 g (0.39 mole) of cysteine hydrochloride and then 27 g (1.17 gram atom) of flaked sodium are gradually added to 1800 ml of liquid ammonia. After the sodium has disappeared, 95 g (0.42 mole) of the bromide obtained as described above and diluted with 100 ml of diethyl ether is added. When the reaction mixture gives a negative thiol reaction, the ammonia is removed and the residue is then dissolved in 500 ml of iced water and filtered. The aqueous solution is thrice extracted with diethyl ether and its pH is brought to 6.5–7 using 5N hydrochloric acid. The product is filtered and washed with water until free from chloride and bromide ions. 89 g of product is finally obtained (yield = 85.5%). M.pt = 202.5° – 203° (Buchi).

Analysis

The calculated and found values for $C_{14}H_{19}O_2NS$ are:
C % calculated : 63.37; found : 63.28
H % calculated : 7.22; found : 7.32
N % calculated : 5.28; found : 5.15
S % calculated : 12.07; found : 12.16

Thin layer chromatography shows only a single spot. $R_f$ = 0.53 (using the same solvent as in Example 1).

EXAMPLE 7

L β-[1-(p-chlorophenyl)ethylthio]α-amino propanoic acid or S-[1-p-chlorophenyl)ethyl] cysteine (LJ 550).

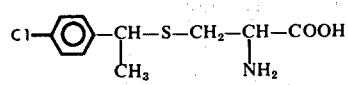

The procedure is the same as that described in Example 7, that is to say 12 g (0.068 mole) of cysteine hydrochloride monohydrate, 4.72 g (0.22 gram atom) of sodium, 200 ml of liquid ammonia and 15 g (0.068 mole) of 1-(p-chlorophenyl)ethyl bromide are reacted together. The product obtained is practically insoluble in all the standard solvents. It is finally washed with acetone and diethyl ether. 11.9 g of product is obtained (yield = 67%). M.pt - 208° – 208.5°C (Buchi).

Analysis

The calculated and found values for $C_{11}H_{14}O_2NS\ Cl$ are:
C % calculated : 50.86; found : 50.52
H % calculated : 5.44; found : 5.44
N % calculated : 5.40; found : 5.50
S % calculated : 12.34; found : 11.98

Thin layer chromatography shows only a single spot. $R_f$ = 0.60 (using the same solvent as that used in Example 1).

EXAMPLE 8

L β-[(pyridyl-3)methylthio]α-amino propanoic acid or S-(pyridyl-3)-methylcysteine (LJ 546).

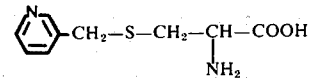

1. (pyridyl-3)methanol hydrochloride

A stream of dry hydrochloric acid is passed through a mixture of 100 g of (pyridyl-3)methanol and 500 ml of absolute ethanol at 0°C. The salt which forms is filtered and rinsed with diethyl ether.

2. (Pyridyl-3)methyl chloride hydrochloride.

37.1 g (0.25 mole) of (pyridyl-3)methanol hydrochloride is added in small quantities to 150 ml of thionyl chloride (distilled over linseed oil) and the mixture is stirred for 90 minutes. When gas is no longer evolved, the mixture is refluxed for 2 hours. 200 ml of dry benzene is added. The precipitate which forms is filtered and washed several times with benzene. The yield of product is quantitative.

M.pt = 142° – 143°C (Buchi) (the product is vesicant).

3. S-[(pyridyl-3)-methyl]cysteine.

17.55 g (0.1 mole) of cysteine hydrochloride monohydrate and 9.2 g (0.4 gram atoms) of sodium are added to 600 ml of liquid ammonia.

After the metal has dissolved, 16.4 g (0.10 mole) of (pyridyl-3)methyl chloride hydrochloride is added in small quantities. After 2 hours the reaction mixture gives a negative thiol reaction. The ammonia is removed and the residue dissolved in 100 ml of iced water. The alkaline solution is then passed through a column of "Dowex 50" and the product eluted with 4N ammonium hydroxide and dried.

The compound is washed with alcohol and then with diethyl ether. 18.05 g of product is obtained (yield = 85%).

M.pt = 204.5° – 205°C
$(\alpha)_D^{20}$ = + 18.7° (2% solution in water).

Analysis

The calculated and found values for $C_9H_{12}O_2N_2S$ are:
C % calculated : 50.97; found : 51.17
H % calculated : 5.70; found : 5.74
N % calculated : 13.20; found : 13.24
S % calculated : 15.11; found : 15.15

Thin layer chromatography shows that the substance forms only a single spot. $R_f$ = 0.49 (using the same solvent as that used in Example 1).

This compound may also be obtained by reaction in an aqueous medium using sodium hydroxide as the acid acceptor instead of liquid ammonia.

The compounds have been subjected to pharmacological tests the results of which are given below:

1. Toxicity

The maximum tolerated doses in the mouse (MTD) when administered by the oral route are given in Table 1 below:

TABLE I

| Compound | MTD | |
|---|---|---|
| LJ 546 | 9 | g/kg |
| LJ 550 | 4 | g/kg |
| LJ 536 | 4 | g/kg |
| LJ 540 | ≥10 | g/kg |
| LJ 545 | ≥10 | g/kg |
| LJ 565 | 1.5 | g/kg |
| LJ 566 | 1.5 | g/kg |
| LJ 558 | 8 | g/kg |

2. Effect on atheromatic deposits in the aorta and on plasma cholesterol in the rabbit In order to create atheromatic lesions experimentally, male albino Bouscat rabbits having an average weight of 2.5 kg are fed on a Provende UAR rabbit diet plus 1 or 2% of cholesterol.

At the end of 11 to 12 weeks, the animals are sacrificed by having their carotid arteries cut after being anaesthetised with Nembutal and the aorta is removed from lowermost point to the iliac fork, cut open longitudinally and spread out upon a cork board. After fixing with formaldehyde and staining with a 2% aqueous solution of acid fuchsin, pearly white atheromatic spots are apparent against the red background which enables the extent of the deposit to be evaluated quantitatively on a scale from 0 to 5 with 0 corresponding to an absence of lesions and 5 to diffuse lipid deposits covering the whole of the endothelium.

After the inside layers of the wall of the aorta have been separated, all the lipids are extracted by the method of Folch et at. The amount of cholesterol is then determined using the Liebermann-Burchard method.

Moreover, a check on the plasma cholesterol is carried out at regular intervals during the test using the Pearson method as adopted to the Technicon auto-analyser by Boy, Bonnafe and Mazet (Applicant's own method).

In a first test, 60 male rabbits each weighing 2.5 kg are fed on the diet detailed below:
  5 weeks : diet containing 2% of cholesterol
  3 weeks : diet containing 1% of cholesterol
  4 weeks : normal diet.

From the beginning the animals are divided into 6 batches of 10 animals each which respectively receive, for the whole duration of the diet, the following products for 5 days per week by the digestive route using an oesophagal probe:
  Batch 1: 10% suspension of gum arabic
  Batch 2: 200 mg/kg of LJ 546 [S-(pyridyl-3-)methyl]cysteine
  Batch 3: 200 mg/kg of LJ 550 (S-[1-(p-chlorophenyl)-ethyl]cysteine)
  Batch 4: 200 mg/kg of LJ 536 (S-cinnamyl cysteine)
  Batch 5: 200 mg/kg of LJ 540 [S-(4-phenyl-3-methylbuten-(3)-yl) cysteine]
  Batch 6: 200 mg/kg of LJ 545 (S-allyl glutathione)

All the products are administered in suspension in the same volume of gum arabic (5 ml).

At the end of 12 weeks, visual examination of the atheromatic lesions in the aorta gave the results shown in Table II, the numerical data giving the average extent of deposit in each batch. The cholesterol levels in the aorta and the plasma are also given in Table II.

TABLE II

| | Extent of atheromatic deposit | Aortic Cholesterol mg/kg | Plasma Cholesterol ml/1000 |
|---|---|---|---|
| Diet only | 3.5 | 20.43 | 1.47 |
| LJ 546 | 1.85 | 10.72 | 0.99 |
| LJ 550 | 2 | 11.90 | 1.17 |
| LJ 536 | 2.05 | 12.21 | 1.20 |
| LJ 540 | 2.60 | 15.00 | 1.29 |
| LJ 545 | 2.70 | 14.38 | 1.36 |

In a second test, using the same experimental method, the two following derivatives were studied in the doses indicated below:
  Batch 1 : 10% suspension of gum arabic
  Batch 2 : 50 mg/kg of LJ 565 (ethyl ester of S-allylcysteine)
  Batch 3 : 50 mg/kg of LJ 566 (isopropyl ester of S-allylcysteine).

The results obtained are given in Table III

TABLE III

| | Extent of atheromatic deposit | Aortic cholesterol mg/kg | Plasma cholesterol ml/1000 |
|---|---|---|---|
| Diet only | 4 | 22.1 | 2.5 |
| LJ 565 | 2.3 | 15 | 2.1 |
| LJ 566 | 2.8 | 17.3 | 2.3 |

CONCLUSIONS

With all these compounds there is observed on the one hand, a reduction in the atheromatic deposits which is apparent upon visual examination and biochemical means and, on the other hand, a reduction in hypercholesterolemia. Compounds LJ 546, LJ 550, LJ 565 and LJ 566 are the most active.

Consequently, the compounds of the invention may be used in human and veterinary medicine as anti-atheromatic agents.

The compounds may be administered in doses of from 200 mg to 3 g per day, preferably 800 mg per day. The compounds may be admixed with conventional solid and liquid pharmacologically acceptable diluents and/or excipients as well as other additives such as lubricants.

Examples of pharmaceutical compositions are as follows:

1. Lozenge Tablets
   LJ 565 — 0.200 g
   Colloidal silica — 0.020 g
   Microcrystalline cellulose — 0.100 g
   Lactose — 0.075 g
   Magnesium stearate — 0.005 g
   — 0.400 g 2. Capsules
   a) LJ 536 — 0.200 g
   Colloidal silica — 0.020 g
   Lactose — 0.055 g
   Talc — 0.025 g
   — 0.300 g b) LJ 540 — 0.200 g
   Colloidal silica — 0.020 g
   Lactose — 0.055 g
   Talc — 0.025 g
   — 0.300 g c) LJ 546 — 0.250 g
   Colloidal silica — 0.010 g
   Talc — 0.015 g
   — 0.275 g 3. Tablets -continued

| a) | LJ 536 | 0.250 g |
| | Colloidal silica | 0.020 g |
| | Microcrystalline cellulose | 0.090 g |
| | Talc | 0.040 g |
| | | 0.400 g |
| b) | LJ 540 | 0.200 g |
| | Colloidal silica | 0.020 g |
| | Microcrystalline cellulose | 0.100 g |
| | Lactose | 0.060 g |
| | Talc | 0.015 g |
| | Magnesium stearate | 0.005 g |
| | | 0.400 g |
| c) | LJ 546 | 0.250 g |
| | Colloidal silica | 0.010 g |
| | Microcrystalline cellulose | 0.120 g |
| | Talc | 0.020 g |
| | | 0.400 g |
| 4. | Injectable Solution | |
| | LJ 546 | 0.200 g |
| | Distilled water q.s. | 10 cm³ |

The pH of the solution of LJ 546 is raised to 7 by the addition of hydrochloric acid. After filtering the solution is inserted into glass ampoules which are sealed and then sterilized in an autoclave.

The cysteine derivatives which form the subject of the present invention may be used to treat the following complaints:

1. all atheromatic complications:
   coronary deficiencies,
   arterial diseases of the lower limbs
   cerebral vascular deficiency (softening, strokes),
   arterial hypertension,
   vascular nephropathy and
   vascular retinopathy
2. disorders of the lipid metabolism:
   hypercholesterolemia and
   hypertriglyceridemia
3. Damage to the basic tissues:
   arthroses,
   bone disease and
   non-atheromatic arterial disease
4. and possibly:
   cicatrization disorders
   fibrosis
   collagenosis
5. Enzyme disease accompanied by pathological amino-aciduria
   homocysteinemia.

We claim:

1. An L S-substituted cysteine derivative of the formula

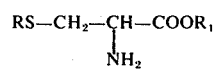

in which R is a substituent selected from the group consisting of allyl, geranyl, cinnamyl, benzylidene-3-butyl and 1-(para-chlorophenyl)ethyl and $R_1$ is selected from the group consisting of hydrogen and alkyl having one to four carbon atoms provided that when R is allyl, $R_1$ is an alkyl group having 1 to 4 carbon atoms, and salts of said derivatives with pharmacologically acceptable organic and mineral acids.

2. The compound of claim 1 in which R is geranyl.
3. The compound of claim 1 in which R is allyl and $R_1$ is ethyl.
4. The compound of claim 1 in which R is allyl and $R_1$ is isopropyl.
5. The compound of claim 1 in which R is allyl.
6. The compound of claim 1 in which R is cinnamyl and $R_1$ is hydrogen.
7. The compound of claim 1 in which R is benzylidene-3-butyl and $R_1$ is hydrogen.
8. The compound of claim 1 in which R is 1-(para-chlorophenyl)ethyl and $R_1$ is hydrogen.

* * * * *